United States Patent [19]

Alban et al.

[11] Patent Number: 5,380,528
[45] Date of Patent: Jan. 10, 1995

[54] SILICONE CONTAINING SKIN CARE COMPOSITIONS HAVING IMPROVED OIL CONTROL

[75] Inventors: Noelle C. Alban, Naugatuck; George E. Deckner, Trumbull, both of Conn.

[73] Assignee: Richardson-Vicks Inc., Shelton, Conn.

[21] Appl. No.: 121,672

[22] Filed: Sep. 15, 1993

Related U.S. Application Data

[63] Continuation of Ser. No. 68,565, May 27, 1993, abandoned, which is a continuation of Ser. No. 621,160, Nov. 30, 1990, abandoned.

[51] Int. Cl.$^6$ ............... A61K 7/48; A61K 9/10
[52] U.S. Cl. ............... 424/401; 424/78.03; 424/486; 424/487; 424/59; 514/864; 514/859; 514/863; 514/873; 514/944; 252/315.1; 252/315.4
[58] Field of Search .......... 424/401, 78.03; 514/844–847, 877, 864

[56] References Cited

U.S. PATENT DOCUMENTS

| | | | |
|---|---|---|---|
| Re. 29,814 | 10/1978 | Snyder | 424/81 |
| 3,855,290 | 12/1974 | Zak et al. | 260/561 B |
| 4,515,784 | 5/1985 | Bogardus et al. | 514/63 |
| 4,529,588 | 7/1985 | Smith et al. | 424/70 |
| 4,534,964 | 8/1985 | Herstein et al. | 424/70 |
| 4,721,769 | 11/1988 | Rubner | 528/75 |
| 4,728,457 | 3/1988 | Fieler et al. | 252/174.15 |
| 4,741,855 | 5/1988 | Grote et al. | 252/142 |
| 4,837,019 | 6/1989 | Georgalas et al. | 424/81 |
| 4,859,456 | 8/1989 | Marschner | 424/47 |
| 4,863,725 | 9/1989 | Deckner et al. | 424/81 |
| 4,960,764 | 10/1990 | Figueroa, Jr. et al. | 514/938 |
| 4,973,473 | 11/1990 | Schneider et al. | 424/63 |
| 4,978,526 | 12/1990 | Gesslein | 424/70 |
| 4,988,503 | 1/1991 | Macchio et al. | 424/63 |
| 5,073,371 | 12/1991 | Turner et al. | 424/401 |
| 5,073,372 | 12/1991 | Turner et al. | 424/401 |

FOREIGN PATENT DOCUMENTS

| | | |
|---|---|---|
| 8319558 | 4/1984 | Australia . |
| 107118 | 5/1984 | European Pat. Off. . |
| 0327379 | 8/1989 | European Pat. Off. . |
| 330369 | 8/1989 | European Pat. Off. . |
| 1211518 | 8/1989 | Japan . |
| 1-250305 | 10/1989 | Japan . |
| 1250305 | 10/1989 | Japan . |
| 2192194 | 11/1988 | United Kingdom . |

Primary Examiner—Edward J. Webman
Attorney, Agent, or Firm—Anthony D. Sabatelli; Leonard W. Lewis; David K. Dabbiere

[57] ABSTRACT

A skin care composition in the form of a substantially oil-free aqueous gel comprising a water-soluble humectant, a hydrophilic gelling agent, a specific silicone component and a specific cationic surfactant component. The compositions provide improved oil control along with improved skin feel and residue characteristics together with excellent moisturizing, emolliency, rub-in and absorption characteristics.

19 Claims, No Drawings

SILICONE CONTAINING SKIN CARE COMPOSITIONS HAVING IMPROVED OIL CONTROL

This is a continuation of application Ser. No. 08/068,565, filed on May 27, 1993, now abandoned, which is a continuation of application Ser. No. 07/621,160, filed on Nov. 30, 1990, now abandoned.

TECHNICAL FIELD

The present invention relates to facial-care cosmetic compositions. In particular it relates to cosmetic compositions in the form of substantially oil-free aqueous gels having improved oil control which provide improved skin feel and residue characteristics together with excellent moisturizing, emolliency, rub-in and absorption characteristics.

BACKGROUND OF THE INVENTION

Sebum, or skin oil, is produced in the sebaceous glands located in the pilosebaceous apparatus of the skin and reaches the skin surface through the duct of the hair follicles. The presence of excessive amounts of sebum on the skin surface often results in an unattractive cosmetic condition commonly known as "oily skin". Sebum also plays an important role in the pathogenesis of ache. Sebaceous gland activity is significantly increased in ache subjects, and individuals with the most severe ache often have the highest sebum secretion rates.

The spreading of sebum on the skin surface is thus an important cosmetic parameter since its distribution on the skin surface can determine the appearance of oiliness or greasiness and can contribute to the severity of ache.

It is advantageous, therefore, to have available means for controlling the distribution of sebum over the surface of human skin, with particular regard to skin characterized by an excessive secretion or presence of sebum upon the surface and to affected skin areas of, for example, ache patients. It is also advantageous to have available a facial care composition which will assist the facial stratum corneum in maintaining their barrier and water retention functions at optimum performance in spite of deleterious interactions which the skin may encounter in washing, work, and recreation.

Many currently marketed facial products do not effectively control the distribution of sebum upon the surface of the skin. Without being limited by theory, it is believed that current leave-on emulsion products undesirably modify the surface properties of the skin, thereby increasing the contact angle of the sebum with the skin and thus preventing its spreading. These products cause the secreted sebum to remain as small discrete droplets upon the skin, thus resulting in oily skin and its attendant problems.

Typically, the problem of oily facial skin has been dealt with by frequent cleansing and the use of astringent preparations. However, such remedies are of questionable efficacy and not always practical, and also have the disadvantage of drying, irritating, and abrading the skin. Additionally, any benefits which may be obtained through cleansing and the use of astringents are only temporary. Once the skin has been cleansed of sebum, the skin begins secreting sebum anew so that the oily skin problem soon returns.

The prior art teaches the incorporation of clays, talcs, silicas, starches, polymers, and other such materials into skin care products for absorbing sebum and controlling oily skin. See U.S. Pat. No. 4,940,578, Yoshihara, T. et al., issued Jul. 10, 1990; U.S. Pat. No. 4,885,109, to Umemoto, I. et al., issued Dec. 5, 1989; U.S. Pat. No. 4,536,399, to Flynn, R. G. et al., issued Aug. 20, 1985; U.S. Pat. No. 4,489,058, to Lay, G. E. et al., issued Dec. 18, 1984; U.S. Pat. No. 4,388,301, to Klein, R. W., issued Jun. 14, 1983; and U.S. Pat. No. 4,000,317, to Merida, W. C. et al., issued Dec. 28, 1976. However, the practicality of incorporating sebum absorbing materials is limited by the sebum absorbing capacity of the material, formulation difficulties, and the negative aesthetic properties which these materials impart to finished products. Also, any oil control benefit which may be obtained is merely temporary.

A longer lasting method of reducing sebum on the skin is through the use of topical or systemic agents believed to provide a sebosuppressive effect. See Karg, G. et al., "Sebosuppression", *Cosmetics & Toiletries*, vol. 102, pp. 140–146 (April 1987); U.S. Pat. No. 4,593,021, to Hsia, S. L. et al., issued Jun. 3, 1986; U.S. Pat. No. 4,587,235, to Bittler, D. et al., issued May 6, 1986; U.S. Pat. No. 4,529,587, to Green, M. R., issued Jul. 16, 1985; U.S. Pat. No. 4,210,654 to Bauer et al., issued Jul. 1, 1980; and U.S. Pat. No. 4,016,287, to Eberhardt et al., issued Apr. 5, 1977. Without being limited by theory, it is believed that sebosuppressive agents decrease the sebum output of the pilosebaceous ducts of the skin, thereby reducing surface oiliness. However, many sebosuppressive agents are potent drugs having undesirable side effects on diuretic activity, inflammation mediators, blood pressure, hormonal levels, cholesterol synthesis, and other bodily functions. Thus, it may not always be practical, desirable, or even possible to utilize sebosuppressive agents to control oily skin.

The control of sebum spreading via topical formulations which do not contain sebosuppressive agents is described in Australian Patent Application 8,319,558 to Herstein et al., published Apr. 12, 1984. This patent discloses formulations for use on oily skin such as cleansers, shampoos, and anti-ache treatments, which contain -gluconamidopropyl dimethyl 2-hydroxyethyl ammonium chloride. However, these formulations have the undesirable characteristic of increasing the contact angle of sebum with the skin and inhibiting the even spreading and distribution of the sebum.

Furthermore, in addition to the limitations of the prior art discussed above, most currently marketed emulsion products actually contribute to and aggravate oily skin problems. Most emulsion products are oil-in-water or water-in-oil emulsions containing high levels of fats and oils. The high levels of fats and oils in these products give them their characteristic heavy and greasy aesthetics and contribute to oily skin problems. The limited number of products which claim to be free from: fats and oils are usually not emulsion type products, but instead are low viscosity, hydro-alcoholic formulations which are too harsh and astringent for regular or frequent use.

Therefore, it would be highly desirable to develop facial compositions which overcome the disadvantages of the prior art. It would also be highly desirable to provide facial compositions which will assist the facial stratum corneum in maintaining their barrier and water retention functions at optimum performance in spite of deleterious interactions which the skin may encounter in washing, work, and recreation.

Conventional cosmetic cream and lotion compositions as described, for example, in Sagatin, *Cosmetics Science and Technology*, 2nd Edition, Volume 1, Wiley Interscience (1972) and *Encyclopedia of Chemical Technology*, Third Edition, Volume 7 are known to provide varying degrees of emolliency, barrier and water-retention (moisturizing) benefits.

Other cosmetic compositions are disclosed in, for example, U.S. Pat. No. 4,837,019 to Georgalas et al., issued Jun. 16, 1989 and also in U.S. Pat. No. 4,863,725 to Decknet et al., issued Sep. 5, 1989, both of which are incorporated by reference herein.

To improve moisturizing benefits water-soluble humectants such as glycerine have been added to cosmetic compositions; however these water-soluble humectants generally significantly increase the tacky feeling. Applicants have found that the use of a specific silicone component along with a specific cationic surfactant component in substantially oil-free aqueous gel-type compositions provides improved oil-control along with significantly improved skin feel and provides a visually appealing product. Further, these compositions, when applied, provide the user with improved make-up application and protection from environmental factors (e.g., irritants such as wind, heat and cold) as well as protection from common household irritants (e.g., cleansers and the like). These substantially oil-free gel-type cosmetic compositions are also particularly useful in warmer climates because they reduce the tack associated with heat and humidity.

The present invention therefore provides substantially oil-free gel-type cosmetic compositions which provide improvements in absorption, residue and skin-feel characteristics without detriment to either short or longer term moisturizing effectiveness or emolliency.

It is therefore an object of the present invention to provide improved facial compositions which provide reduced tack and provide the user a smoother skin feel and which reduce the oily appearance and greasy feel of facial skin and control the distribution of sebum upon the skin surface. It is still another object of the present invention to provide compositions which are aesthetically pleasing and substantially free from fats and oils. It is yet another object of the present invention to provide compositions for controlling sebum distribution without incorporating oil-absorbing materials. It is a further object of the present invention to provide oil-free moisturization to minimize skin regreasing over time. It is still a further object to provide skin care compositions which, when applied, provide improved make-up application as well as improved protection from environmental and common household irritants.

These and other objects of this invention will become apparent in light of the following disclosure.

SUMMARY OF THE INVENTION

Accordingly, the present invention provides a skin care composition in the form of a substantially oil-free aqueous gel comprising:

(a) from 0.5% to 20% by weight of a water-soluble humectant;

(b) from 0.1% to 20% by weight of a hydrophilic gelling agent;

(c) from 1.0% to 10% by weight of a silicone component consisting essentially of i) a silicone gum having a molecular weight of from about 200,000 to about 540,000 selected from the group consisting of dimethiconol, fluorosilicone, dimethicones or mixtures thereof; and ii) a silicone-based carrier having a viscosity from about 0.65 cps. to about 100 cps.

wherein the ratio of i) to ii) is from about 10:90 to about 20:80, preferably from about 13:87 to about 17:83, and wherein said component has a final viscosity of from about 500 cps. to about 10,000 cps. preferably from about 1,000 cps. to about 5,000 cps.; and (d) from 0.01 to 5% of a cationic surfactant.

All percentages and ratios used herein are by weight, and all measurements are at 25° unless otherwise indicated.

DETAILED DESCRIPTION OF THE INVENTION

The compositions of the present invention contain four essential ingredients as well as various optional components as indicated below. All levels and ratios are by weight of total composition, unless otherwise indicated.

Water-soluble Humectant

A first essential ingredient is a water-soluble humectant. Most preferred for use herein is glycerine (sometimes know as glycerol or glycerin) and derivatives thereof (e.g., propoxylated glycerine and ethoxylated glycerine). Chemically, glycerine is 1,2,3-propanetriol and is a product of commerce. One large source of the material is as a byproduct in the manufacture of soap.

Other useful humectants include D-panthenol, hyaluronic acid, glucosides (e.g., Glucam E10 and E20 available from Amerchol Corporation), lactamide monoethanolamine, and acetamide monoethanolamine.

Mixtures of these water-soluble humectants can also be used.

In the present invention the water-soluble humectant, is present at a level of from about 0.5% to about 20%, preferably from about 1% to about 10%, more preferably from about 4% to about 8% by weight of the composition.

Hydrophilic Gelling Agent

The compositions of the present invention also contain a hydrophilic gelling agent at a level preferably from about 0.1% to about 20%, more preferably from about 0.2% to about 2%, and most preferably from about 0.3% to about 1%. The gelling agent preferably has a neutralized viscosity (1% aqueous solution, 20° C., Brookfield RVT) of at least about 4000 cps, more preferably at least about 10,000 cps, and most preferably at least about 50,000.

Suitable hydrophilic gelling agents can generally be described as water-soluble or colloidally water-soluble polymers, and include cellulose ethers (e.g. hydroxyethyl cellulose, methyl cellulose, hydroxy propylmethyl cellulose), polyvinylpyrrolidone, polyvinylalcohol, guar gum, hydroxypropyl guar gum and xanthan gum.

Also useful in the compositions of the present invention are carboxylic acid copolymers. These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

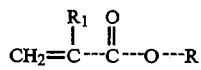

wherein R is an alkyl radical containing 10 to 30 carbon atoms and $R_1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking polyalkenyl polyether monomer is from about 0.2 to 0.4 weight percent. The preferred cross-linking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

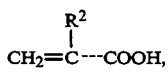

wherein $R^2$ is a substituent selected from the class consisting of hydrogen, halogen, and the cyanogen ($-C\equiv N$) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which may be present in the polymers include polyfunctional vinylidene monomers containing at least two terminal $CH_2<$ groups, including for example, butadiene, isoprene, divinyl benzene, divinyl naphthlene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, acrylates/C10-30 alkyl acrylate cross polymer, (available as Carbopol 934, Carbopol 941, Carbopol 950, Carbopol 951, Carbopol 954, Carbopol 980, Carbopol 981, Carbopol 1342, and the Pemulen series, respectively, from B.F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by Lipo Chemicals Inc. under the trademark of HYPAN hydrogels. These hydrogels consist of crystalline plicks of nitriles on a C—C backbone with various other pendant groups such as carboxyls, amides, and amidines. An example would include HYPAN SA100 H, a polymer powder available from Lipo Chemical.

Neutralizing agents suitable for use in neutralizing acidic group containing copolymers herein include sodium hydroxide, potassium hydroxide, ammonium hydroxide, monoethanolamine, diethanolamine, triethanolamine, tetrahydroxypropyl ethylenediamine (available as the Quadrol ® series from BASF), tris, arginine, triisopropylamine and lysine.

The carboxylic acid copolymers can be used individually or as a mixture of two or more polymers and comprise from about 0.025 to about 0.75, preferably from about 0.05 to about 0.25 and most preferably from about 0.075 to about 0.175 percent of the compositions of the present invention.

For the present invention the weight ratio of carboxylic acid copolymer to cationic surfactant is preferably from about 1:10 to about 10:1.

Neutralizing agents suitable for use in neutralizing acidic group containing hydrophilic gelling agents herein include sodium hydroxide, potassium hydroxide, ammonium hydroxide, monoethanolamine, diethanolamine, triethanolamine, tetrahydroxypropyl ethylenediamine (available as the Quadrol ® series from BASF), tris, arginine, triisopropylamine and lysine.

Silicone Component

The present invention comprises from 1.0% to 10% by weight of a silicone component consisting essentially of i) a silicone gum having a molecular weight of from about 200,000 to about 540,000 selected from the group consisting of dimethiconol, fluorosilicone and dimethicones or mixtures thereof; and ii) a silicone-based carrier having a viscosity from about 0.65 cps. to about 100 cps. and wherein the ratio of i) to ii) is from about 10:90 to about 20:80, preferably from about 13:87 to about 17:83, and wherein said component has a final viscosity of from about 500 cps. to about 10,000 cps. preferably from about 1,000 cps. to about 5,000 cps.

The dimethiconol component of the present invention has the chemical structure of

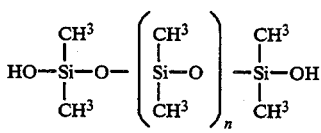

where n is from about 2700 to about 4500, preferably from about 3200 to about 4300 and most preferably n is from about 4000 to about 4300. The dimethiconol component has a molecular weight of from about 200,000 to about 300,000, preferably From about 240,000 to about 260,000 and most preferably about 250,000.

The fluorosilicones useful in the present invention have a molecular weight of front about 200,000 to about 300,000, preferably from about 240,000 to about 260,000 and most preferably about 250,000.

The dimethicones of the present invention are silicone gums. These silicone gums are described by Petrarch and others including U.S. Pat. No., 4,152,416, May 1, 1979 to Spitzer, et al. and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. "Silicone gum" materials useful herein denote high molecular weight materials having a molecular weight of from about 200,000 to about 600,000. Specific examples include polydimethylsiloxane, (polydimethylsiloxane) (methylvinylsiloxane) copolymer, poly(dimethyl siloxane) (diphenyl) (methyl vinyl siloxane) copolymer and mixtures thereof.

The silicone-based carriers of the present invention are certain silicone fluids.

The silicone fluid may be either a polyalkyl siloxane, a polyaryl siloxane, a polyalkylaryl siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the matrix. This is the meaning of "insoluble" as used hereinbefore and hereinafter.

The polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The polyalkylaryl siloxane fluids that may be used include, for example, polymethylphenylsiloxanes have viscosities of about 0.65 to 30,000 centistokes at 25° C. These siloxanes are available, for example, from the General Electric Company as SF 1075 methyl phenyl fluid or from Dow Corning as 556 Cosmetic Grade Fluid.

Also suitable for use are certain volatile cyclic polydimethyls siloxanes of the formula:

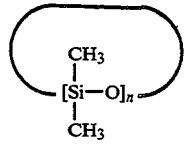

wherein n equals about 3 to about 7.

The viscosity can be measured by means of a glass capillary viscometer as set forth in Dow Corning Corporate Test Method CTM0004, Jul. 29, 1970. Preferably the viscosity ranges from about 350 centistokes to about 100,000 centistokes.

The most preferred silicone component for use herein is a dimethiconol gum having a molecular weight of from about 240,000 to about 260,000 along with a silicone carrier with a viscosity of about 5 cs. An example of this silicone component is Dow Q2-1403 fluid (85% 5cs Dimethyl Fluid/15% Dimethiconol) available from Dow Corning.

Cationic Surfactant

An essential component of the present compositions is a cationic surfactant which is present at a level of from about 0.01% to about 5%, more preferably from about 0.01% to about 2%, and most preferably from about 0.01% to about 1%. McCutcheon's, *Detergents and Emulsifiers*, North American Edition (1986), published by Allured Publishing Corporation, which is incorporated herein by reference, includes a broad listing of cationic surfactants.

Examples of such useful cationic surfactants include distearyl dimethyl ammonium chloride, dilauryl dimethyl ammonium chloride, N-cetyl pyridinium bromide, alkyl dimethyl ethylbenzyl ammonium cyclohexyl sulfamate, dodecyl dimethyl ethylbenzyl ammonium chloride, alkyl triethanolammonium chloride, dimethyl di(hydrogenated tallow) ammonium chloride, Quaternium-15, bis(hydrogenated tallow alkyl) dimethyl methyl sulfates, -gluconamidopropyldimethyl-2-hydroxyethyl ammonium chloride, decyl dimethyl octyl ammonium chloride, dimtheyl 2-hydroxyethyl minkamidopropyl ammonium chloride, Quaternium-18 Methosulfate, isododecylbenzyl triethanolammonium chloride, cocamidopropyl dimethyl acetamido ammonium chloride, Quaternium-45, Quaternium-51, Quaternium-52, Quaternium-53, bis(N-hydroxyethyl-2-oleyl imidazolinium chloride) polyethylene glycol 600, lanolin/isosteramidopropyl ethyl dimethyl ammonium ethosulfate, bis[amidopropyl-N,N-dimethyl-N-ethyl) ammonium methosulfate]dimer acid, Quaternium-62, Quaternium-63, stearamidopropyl dimethyl (myristyl acetate) ammonium chloride, and Quaternium-71. These hydrophobic cationic surfactants can be used either singly or as a combination of one or more materials.

The preferred cationic surfactants for use in this invention are the halide salts of N,N,N-trialkylaminoalkylene gluconamides having the formula:

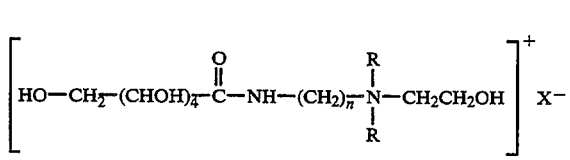

wherein R=alkyl, X=Cl⁻ or Br⁻, and n is an integer from 2 to 4.

Most preferred for use in this invention is γ-gluconamidopropyl dimethyl 2-hydroxyethyl ammonium chloride (CTFA designation Quaternium-22) which has the following structure:

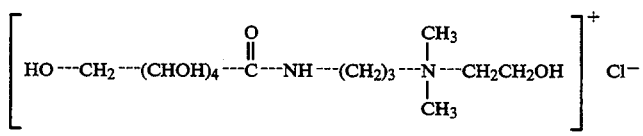

This compound is commercially available as a free-flowing, 60% aqueous solution from Van Dyk, Inc. (Belleville, N.J.) under the trademark Ceraphyl® 60. U.S. Pat. No. 3,855,290 to Zak et al., issued Dec. 17, 1974; U.S. Pat. No. 3,766,267 to Zak et al., issued Oct. 16, 1973; and U.S. Pat. No. 4,534,964 to Herstein et al., issued Aug. 13, 1985, which are all incorporated herein by reference, further describe Quaternium-22 and its use in personal care products.

Optional Components

Polyglycerylmethacrylate. A highly preferred optional component is a water soluble polyglycerylmethacrylate lubricant. This generally should have a viscosity (10% aqueous solution, 20° C., Brookfield RVT) of less than about 4000 cps. preferably less than about 1000 cps and more preferably less than about 500 cps. In additions, the polyglycerylmethacrylate lubricant preferably also has a viscosity (neat) in the range of from about 200 to about 5000 cps (Brookfield RVT, 20° C.), more preferable from about 500 to about 200 cps and especially from about 700 to about 900 cps.

The polyglycerylmethacrylate lubricants which can be used in the compositions of this invention are available under the trademark Lubrajel (RTM) from Guardian Chemical Corporation, 230 Marcus Blvd., Hauppage, N.Y. 11787. In general, Lubrajels can be described as hydrates or clathrates which are formed by the reaction of sodium glycerate with a methacrylic acid polymer. Thereafter, the hydrate or clathrate is stabilized with a small amount of propylene glycol, followed by controlled hydration of the resulting product. Lubrajels are marketed in a number of varying glycerate:polymer ratios and viscosities. Preferred for use herein, however, is so-called Lubrajel Oil, which has a typical viscosity of about 800 cps. Another preferred lubricant is Lubrajel DV which has a typical viscosity of 380,000 cps. Other suitable Lubrajels include Lubrajel TW, Lubrajel CG and Lubrajel MS.

In the present compositions, the polyglycerylmethacrylate is incorporated at a level of -from about 0.1% to about 20%, preferably from about 0.2% to about 2%, and more preferably from about 0.3% to about 1% by weight of the composition.

A number of additional water-soluble materials can be added to the compositions of the present invention. Such materials include the other humectants such as sorbitol, propylene glycol, ethoxylated glucose and hexanetriol; keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl(RTM)K400, Bromopol (2-bromo-2-nitropropane-1,3-diol), phenoxypropanol, DMDM Hydantoin/3-Iodo-2-Propynyl Butyl Carbamate (available as Glydant ® and Glydant Plus®); anti -bacterials such as Irgasan (RTM) and phenoxyethanol (preferably at levels of from 0.5% to about 5%); soluble or colloidally soluble moisturizing agents such as hyaluronic acid, chitosan, and starch-grafted sodium polyacrylates such Sanwet (RTM) IM-1000, IM-1500 and IM-2500 available from Celanese Superabsorbent Materials Portsmith, Va., USA and described in U.S. Pat. No. 4,076,663; coloring agents; perfumes and perfume solubilizers etc. Highly preferred for use herein are alcohols (e.g., ethanol). Water is also present at a level of from about 50% to about 99.3%, preferably from about 80% to about 95% by weight of the compositions herein.

Pharmaceutical Actives. Pharmaceutical actives useful in the present invention include any chemical material or compound suitable for topical administration which induces any desired local or systemic effect. These actives are present at a level from about 0.1% to about 20%. Such substances include, but are not limited to antibiotics, antiviral agents, analgesics, antihistamines, antiinflammatory agents, antipruritics, antipyretics, anesthetic agents, diagnostic agents, hormones, antifungals, antimicrobials, cutaneous growth enhancers, pigment modulators, antiproliferatives, antipsoriatics, retinoids, anti-ache medicaments (e.g. benzoyl peroxide, sulfur, etc.), antineoplastic agents, phototherapeutic agents, and keratolytics (e.g. resorcinol, salicylic acid) and sunscreens.

Vitamins. Various vitamins may also be included in the compositions of the present invention. For example, Vitamin A, and derivatives thereof, ascorbic acid, Vitamin B, biotin, panthothenic acid, Vitamin D, and mixtures thereof may be used. Vitamin E, tocopherol acetate and derivatives may also be used.

Other Optional Components. A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

The present compositions of the invention are in aqueous gel form and are preferably formulated so as to have product viscosity of at least about 4,000 and preferably in the range from about 4,000 to about 300,000 cps, more preferable from about 20,000 to about 200,000 cps and especially from about 80,000 to about 150,000 cps (20° C., neat, Brookfield RVT). Preferably the compositions are visually translucent. The compositions are also substantially free of oil, i.e. contain less than about 1%. and preferably less than about 0.1% of materials which are insoluble or which are not colloidally soluble in the aqueous gel matrix at 10° C. "Colloidally-soluble" herein refers to particles in the usual colloidal size range, typically from 1 to 1000 nm, especially from 1 to 500 nm. In highly preferred embodiment, the compositions are substantially free of materials which are insoluble or not colloidally soluble in distilled water at 20° C. Such materials include many conventional emollient materials such as hydrocarbon oils and waxes, glyceride esters, alkyl esters, alkenyl esters, fatty alcohols, certain fatty alcohol ethers and fatty acid esters of ethoxylated fatty alcohols, sterols extracted from lanolin, lanolin esters, wax esters, beeswax derivatives, vegetable waxes, phospholipids, sterols and amides. The compositions can, however, contain low levels of insoluble ingredients added, for example for visual effect purposes, e.g. thermochromic liquid crystalline materials such as the microencapsulated cholesteryl esters and chiral nematic (nonsterol) based chemicals such as the (2-methylbutyl) phenyl 4-alkyl (oxy)benzoates available from Hallcrest, Glenview, Ill. 60025, U.S.A.

The compositions of the invention have no need of and are preferably also substantially free of anionic and other non-ionic surfactant materials which are conventionally added to cosmetic cream and lotion compositions in order to emulsify a water-insoluble oily phase. Again, "substantially free" means less than about 1%, preferably less than about 0.1% of the indicated materials. Such emulsifiers include ethoxylated fatty acids, ethoxylated esters, phosphated esters, ethoxylated fatty alcohols, polyoxyethylene fatty ether phosphates, fatty acid amides, alkyl lactylates, soaps, alkyl polyglucosides, allyl sucrose esters, allyl polyglycerol esters, etc. The pH of the compositions is preferably from about 4 to about 9, more preferably from about 6.5 to about 8.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE 1

A substantially oil-free aqueous skin care gel is made by combining the following ingredients utilizing conventional mixing techniques.

| Ingredient | % W/W |
|---|---|
| Alcohol SD-40 | 5.0 |
| Glycerine | 3.0 |
| Hexylene Glycol | 1.0 |
| Carbomer 980[1] | 0.5 |
| Quaternium-22[2] | 0.25 |
| DL-Panthenol | 0.5 |
| Sodium hydroxide | 0.175 |
| DMDM Hydantoin/3-Iodo-2-Propynyl Butyl Carbamate[3] | 0.1 |
| Disodium EDTA | 0.02 |
| Citric Acid | 0.01 |
| 85% 5 cs Dimethyl Fluid/15% Dimethiconol[4] | 3.0 |
| Deionized Water | q.s. |

[1]Carbopol 980 available from B. F. Goodrich
[2]Ceraphyl 60 availalbe from Van Dyk
[3]Glydant Plus available from Lonza
[4]Dow Q2-1403 Fluid available from Dow Corning A preservative premix is made by combining Distilled water, Hexylene Glycol, DMDM Hydantoin/3-Iodo-2-Propynyl Butyl Carbamate in a weight/weight (w/w) ratio of 1:1:0.1, respectively. Separately, a 10% w/w solution of DL Panthenol and NaOH is made. Using a Lightnin' Mixer with a 3 blade paddle prop, the Carbomer is dispersed into the water. The Disodium EDTA and Citric Acid are then added. The resultant combination is mixed until the Carbomer is evenly dispersed (approx. 10–15 min for a 1 kg batch). The preservative premix, Quaterium-22, alcohol SD-40, is added under continued mixing. The prop on the Lightnin' Mixer is changed to a high lift prop. While mixing, Glycerin, DL-Panthenol solution, and 85% 5 cs Dimethyl Fluid/15% Dimethiconol are added. The result in mixture is mixed and NaOH is added to the solution. The solution is mixed for an additional 5–10 minutes.

The composition is useful for providing control of the distribution of sebum on the skin and provides improved skin feel and residue characteristics together with excellent moisturizing, emolliency, rub-in and absorption characteristics.

Example II

A substantially oil-free aqueous skin care gel is made by combining the following ingredients utilizing conventional mixing techniques as described above in Example I.

| Ingredient | % W/W |
|---|---|
| Glycerine | 2.0 |
| Hydrogenated Glucose Syrup[1] | 1.0 |
| Butylene Glycol | 1.0 |
| DL-Panthenol | 1.0 |
| Quaternium-22 | 0.25 |
| Polyglyceryl methacrylate[2] | 15.0 |
| DMDM Hydantoin/3-Iodo-2-Propynyl Butyl Carbamate[3] | 0.1 |
| Disodium EDTA | 0.02 |
| 85% 5 cs Dimethyl Fluid/15% Dimethiconol[4] | 3.0 |
| Deionized Water | q.s. |

[1]Hystar CG available from Lonza
[2]Lubrajel DV available from Freeman, Inc.
[3]Glydant Plus available from Lonza
[4]Dow Q2-1403 Fluid available from Dow Corning The composition is useful for providing control of the distribution of sebum on the skin and provides improved skin feel and residue characteristics together with excellent moisturizing, emolliency, rub-in and absorption characteristics.

EXAMPLES III–VI

Substantially oil-free aqueous skin care gels are made by combining the following ingredients utilizing conventional mixing techniques as described above in Example I.

| Ingredient | % W/W | | | |
|---|---|---|---|---|
| | III | IV | V | VI |
| Glycerin | 3.0 | 3.0 | 3.0 | 3.0 |
| Hexylene Glycol | 1.0 | 1.0 | 1.0 | 1.0 |
| Carbomer 980[1] | 0.5 | 0.5 | 0.5 | 0.5 |
| Quaternium-22 | 0.25 | 0.25 | 0.25 | 0.25 |
| DL-Panthenol | 0.5 | 0.5 | 0.5 | 0.5 |
| Sodium Hydroxide | 0.175 | 0.175 | 0.175 | 0.175 |
| DMDM Hydantoin/3-Iodo-2-Propynyl Butyl Carbamate[2] | 0.1 | 0.1 | 0.1 | 0.1 |
| Disodium EDTA | 0.02 | 0.02 | 0.02 | 0.02 |
| Citric Acid | 0.01 | 0.01 | 0.01 | 0.01 |
| Polyglycerylmethacrylate[3] | 0.5 | — | — | — |
| 85% 5 cs Dimethyl Fluid/15% Dimethiconol[4] | 3.0 | 5.0 | — | — |
| 85% 5 cs Dimethyl Fluid/15% Dimethiconol Gum[5] | — | — | 3.0 | 5.0 |
| Deionized Water | To 100 | | | |

[1]Carbopol 980 available from B. F. Goodrich
[2]Glydant Plus available from Lonza
[3]Lubrajel Oil available from Freeman, Inc.
[4]Dow Q2-1403 Fluid available from Dow Corning
[5]GE SF 1236 Fluid available from General Electric The compositions are useful for providing control of the distribution of sebum on the skin and provide improved skin feel and residue characteristics together with excellent moisturizing, emolliency, rub-in and absorption characteristics.

What is claimed is:

1. A skin care composition in the form of an aqueous gel containing less than about 1% of a hydrocarbon oil or wax comprising:
   (a) from about 0.5% to about 20% by weight of a water-soluble humectant;
   (b) from about 0.1% to about 20% by weight of a hydrophilic gelling agent;
   (c) from about 1.0% to about 10% by weight of a silicone component consisting essentially of
   i) a dimethiconol of the formula:

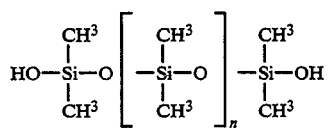

where n is from about 2700 to about 4500, and wherein the molecular weight is from about 200,000 to about 300,000; and
   ii) a silicone fluid carrier having a viscosity from about 0.65 cps. to about 100 cps.
   wherein the ratio of i) to ii) is from about 10:90 to about 20:80 and wherein said component has a final viscosity of from about 500 cps. to about 10,000 cps.; and
   (d) from about 0.01 to about 5% of a cationic N,N,N-trialkylaminoalkylene gluconamide surfactant of the formula

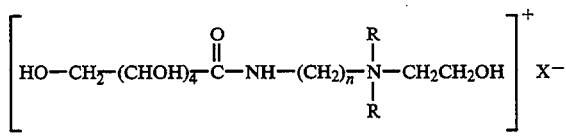

wherein R=alkyl, X=Cl$^-$ or Br$^-$, and n is an integer from 2 to 4.

2. A composition according to claim 1 wherein the dimethiconol component has a molecular weight of from about 240,000 to about 260,000 and n is from about 3200 to about 4500.

3. A method for controlling sebum distribution on facial skin, said method comprising topically applying to the facial skin an effective amount for controlling sebum, distribution of a substantially oil-free aqueous gel composition according to claim 2.

4. A composition according to claim 2 wherein the dimethicone has a molecular weight of from about 480,000 to about 520,000 and wherein the cationic surfactant is γ-glyconamidopropyl dimethyl 2-hydroxyethyl ammonium chloride.

5. A composition according to claim 4 wherein the silicone carrier is a non-volatile silicone fluid selected from the group consisting of polyalkyl siloxanes, polyaryl siloxanes, polyalkylaryl siloxanes, polyether siloxanes, and mixtures thereof.

6. A composition according to claim 5 which further comprises from 0.1% to 10% by weight of a water-soluble polyglycerylmethacrylate lubricant having a viscosity (10% aqueous solution, 20° C., Brookfield RVT) of less than 30,000 cps, and comprising from 1% to 10% by weight of glycerine.

7. A composition according to claim 6 wherein the polyglycerylmethacrylate lubricant is a hydrate or clathrate formed by the reaction of sodium glycerate with a methacrylic acid polymer.

8. A composition according to claim 7 wherein the hydrophilic gelling agent is present a level from about 0.2% to about 2% and has a neutralized viscosity of at least about 10,000 cps.

9. A method for controlling sebum distribution on facial skin, said method comprising topically applying to the facial skin an effective amount for controlling sebum distribution of a substantially oil-free aqueous gel composition according to claim 8.

10. A composition according to claim 8 comprising from 0.3% to 1% by weight of the polyglycerylmethacrylate lubricant.

11. A composition according to claim 10 having a viscosity (20° C., neat, Brookfield RVT) of from 4000 to 300,000 cps.

12. A composition according to claim 11 wherein the neutralized gelling agent has viscosity (1% aqueous solution, 20° C., Brookfield RVT) of at least 80,000 cps.

13. A composition according to claim 12 wherein the gelling agent is a colloidally water-soluble carboxyvinyl polymer of acrylic acid cross-linked with from about 0.2% to 0.4% of a cross-linking agent selected from allylpentaerythritol, trimethylolpropane diallylether, and allyl sucrose.

14. A composition according to claim 13 wherein the carboxylic acid copolymer is selected from the group consisting of carbomer, acrylates/C10–30 alkyl acrylate crosspolymer, and mixtures thereof.

15. A method for controlling sebum distribution on facial skin, said method comprising topically applying to the facial skin an effective amount for controlling sebum distribution of a substantially oil-free aqueous gel composition according to claim 14.

16. A composition according to claim 14 wherein the weight ratio of carboxylic acid copolymer to gluconamide is from about 1:10 to about 10:1.

17. A method for controlling sebum distribution on facial skin, said method comprising topically applying to the facial skin an effective amount for controlling sebum distribution of a substantially oil-free aqueous gel composition according to claim 16.

18. A composition according to claim 16 wherein said emulsion further comprises from about 0.1% to about 20% of a pharmaceutical active.

19. A method for controlling sebum distribution on facial skin, said method comprising topically applying to the facial skin an effective amount for controlling sebum distribution of a substantially oil-free aqueous gel composition according to claim 1.

* * * * *

UNITED STATES PATENT AND TRADEMARK OFFICE
CERTIFICATE OF CORRECTION

PATENT NO. : 5,380,528

DATED : January 10, 1995

INVENTOR(S) : Noelle C. Alban et al.

It is certified that error appears in the above-identified patent and that said Letters Patent is hereby corrected as shown below:

At column 1, line 29 "ache" should read --acne--.

At column 1, line 30 "ache" should read --acne--.

At column 1, line 31 "ache" should read --acne--.

At column 1, line 37 "ache" should read --acne--.

At column 1, line 43 "ache" should read --acne--.

At column 2, line 10 "Merida" should read --Menda--.

At column 2, line 44 "anti-ache" should read --anti-acne--.

At column 2, line 59 "from: fats" should read --from fats--.

At column 3, line 4 "Sagatin" should read --Sagarin--.

At column 3, line 13 "Decknet" should read --Deckner--.

At column 4, line 4 "dimethicones or mixtures" should read --dimethicones, and mixtures--.

At column 7, line 13 "preferably From" should read --preferably from--.

At column 7, line 16 "of front about" should read --of from about--.

At column 7, lines 33-34 "poly(dimethyl siloxane)" should read --poly(dimethylsiloxane)--.

At column 7, line 34 "(methyl vinyl siloxane)" should read --(methylvinylsiloxane)--.

At column 7, line 60 "polydimethyls siloxanes" should read --polydimethylsiloxanes--.

At column 8, line 33 "Quatermium-15" should read --Quaternium-15--.

At column 9, line 22 "cps. preferably" should read --cps, preferably--.

At column 9, line 47 "of -from" should read --of from--.

UNITED STATES PATENT AND TRADEMARK OFFICE
CERTIFICATE OF CORRECTION

PATENT NO. : 5,380,528

DATED : January 10, 1995

INVENTOR(S) : Noelle C. Alban et al.

It is certified that error appears in the above-identified patent and that said Letters Patent is hereby corrected as shown below:

At column 9, line 66 "hyaluronic" should read --hylaronic--.

At column 10, line 27 "anti-ache" should read --anti-acne--.

At column 10, line 28 "antineoplastic" should read --antineoplastics--.

At column 10, line 55 "1%. and" should read --1%, and--.

At column 11, line 18 "alcohols. polyoxyethylene" should read --alcohols, polyoxyethylene--.

At column 13, line 52 "sebum, distribution" should read --sebum distribution--.

Signed and Sealed this

Twenty-fifth Day of May, 1999

Attest:

Q. TODD DICKINSON

*Attesting Officer*  *Acting Commissioner of Patents and Trademarks*